United States Patent
Kuechler et al.

(10) Patent No.: US 7,332,639 B2
(45) Date of Patent: Feb. 19, 2008

(54) PROCESS FOR PRODUCING OLEFINS

(75) Inventors: Keith H. Kuechler, Friendswood, TX (US); Jeffrey L. Brinen, League City, TX (US); Philip A. Ruziska, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 750 days.

(21) Appl. No.: 10/871,394

(22) Filed: Jun. 18, 2004

(65) Prior Publication Data

US 2005/0283038 A1    Dec. 22, 2005

(51) Int. Cl.
*C07C 7/00* (2006.01)
*C07C 1/00* (2006.01)

(52) U.S. Cl. .................. 585/809; 585/802; 585/639; 585/640

(58) Field of Classification Search ............. 585/809, 585/802, 639, 638
See application file for complete search history.

(56) References Cited

U.S. PATENT DOCUMENTS

| | | | | |
|---|---|---|---|---|
| 6,121,504 | A | 9/2000 | Kuechler et al. | 585/640 |
| 6,303,841 | B1 | 10/2001 | Senetar et al. | 585/639 |
| 6,403,854 | B1 | 6/2002 | Miller et al. | 585/638 |
| 6,459,009 | B1 | 10/2002 | Miller et al. | 585/809 |
| 2002/0007101 | A1 | 1/2002 | Senetar et al. | 585/809 |
| 2003/0130555 | A1 | 7/2003 | Cheng et al. | 585/804 |

FOREIGN PATENT DOCUMENTS

| DE | 199 11 910 | 9/2000 |
|---|---|---|
| DE | 101 50 480 | 4/2003 |

OTHER PUBLICATIONS

U.S. Appl. No. 10/720,505, filed Nov. 24, 2003, (Inventors: Keith Kuechler, Jeffrey L. Brinen, James Lattner, & Allen S. Gawlik, entitled "Recycling Oxygenate-Rich Streams In Oxygenate-To-Olefin Processes".
English Abstract for DE 101 50 480, "*Procedure for the Removal of Oxygenates from an Olefin-Containing Product Stream*", Apr. 17, 2003.
English Abstract for DE 199 11 910, "*Liquid-Liquid Extraction and Azeotropic Distilliation for Separation of Oxygen-Containing Compounds from Fischer-Tropsch Main Product*", Sep. 21, 2000.

*Primary Examiner*—Glenn Caldarola
*Assistant Examiner*—In Suk Bullock

(57) ABSTRACT

A process is described for producing an olefins stream from a first vapor effluent stream from an oxygenate to olefin conversion reaction, said first vapor effluent stream comprising $C_2$ and $C_3$ olefins, $C_4$ hydrocarbons, and $C_2$ to $C_6$ carbonyl compounds. In the process, the temperature and pressure of the first vapor effluent stream are adjusted to produce a second vapor effluent stream having a pressure ranging from about 100 psig to about 350 psig (790 to 2514 kPa) and a temperature ranging from about 70° F. to about 120° F. (21 to 49° C.), said second vapor effluent stream containing about 50 wt. % or more $C_4$ hydrocarbons based upon the total weight of $C_4$ hydrocarbons in the first vapor effluent stream. The second vapor effluent stream is then washed with a liquid alcohol-containing stream to produce a third vapor effluent stream, whereafter the third vapor effluent stream is washed with liquid water to provide a fourth vapor effluent stream comprising the $C_2$ and $C_3$ olefins and about 1.0 wt. % or less $C_2$ to $C_6$ carbonyl compounds.

85 Claims, 1 Drawing Sheet

PROCESS FOR PRODUCING OLEFINS

FIELD OF THE INVENTION

The present invention relates to a process for producing olefins and, in particular, ethylene and/or propylene.

BACKGROUND OF THE INVENTION

Olefins are traditionally produced from petroleum feedstocks by catalytic or steam cracking processes. These cracking processes, especially steam cracking, produce light olefin(s), such as ethylene and/or propylene, from a variety of hydrocarbon feedstocks. Ethylene and propylene are important commodity petrochemicals useful in a variety of processes for making plastics and other chemical compounds.

The petrochemical industry has known for some time that oxygenates, especially alcohols, are convertible into light olefin(s). There are numerous technologies available for producing oxygenates including fermentation or reaction of synthesis gas derived from natural gas, petroleum liquids or carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Other known syngas production processes include conventional steam reforming, autothermal reforming, or a combination thereof.

The preferred process for converting an oxygenate, such as methanol, into one or more olefin(s), primarily ethylene and/or propylene, involves contacting the feedstock with a catalyst composition, typically containing a molecular sieve catalyst. The effluent produced by such a process is a complex mixture comprising the desired light olefins, unconverted oxygenates, by-product oxygenates, heavier hydrocarbons and large amounts of water. The separation and purification of this mixture to recover the light olefins and other valuable by-products is critical to the overall efficiency and cost effectiveness of the process. In particular, it is important that the purification scheme produces products that are substantially free of impurities, which could adversely effect downstream processing.

For example, certain oxygenate components present in the effluent from an oxygenate conversion process, particularly aldehydes and ketones, may cause problems in olefin recovery operations and in derivative manufacturing processes that feed and react $C_4+$ hydrocarbons. There is therefore a need to ensure that the effluent purification scheme effectively removes aldehydes and ketones from the olefinic and $C_4+$ hydrocarbon components while at the same time minimizing loss of useful product.

U.S. Pat. No. 6,303,841 and U.S. Patent Application Publication No. 2002/0007101, published Jan. 17, 2002, disclose a process for producing ethylene from oxygenates in which the oxygenate conversion effluent stream is compressed in a multi-stage compressor to a pressure of 1050 to 2860 kPa (150 to 400 psia), preferably 1750 to 2450 kPa (250 to 350 psia), washed with methanol and then water to remove unreacted oxygenates and then contacted with caustic to remove carbon dioxide. The carbon dioxide depleted stream is dried with a solid desiccant and passed to a deethanizer zone to provide a light hydrocarbon feedstream comprising hydrogen, methane, ethylene and ethane, and a deethanized stream comprising propylene, propane, and $C_4+$ olefins. The light hydrocarbon stream is passed to a demethanizer zone operating at a temperature greater than 45° C. to provide a bottom stream comprising ethylene and ethane and an overhead stream comprising hydrogen, methane, and ethylene. The bottom stream is fed to a $C_2$ splitter zone to produce the ethylene product stream and an ethane stream, whereas the overhead stream is fed to a pressure swing adsorption zone to remove hydrogen and methane and produce an ethylene-containing stream which is combined with the oxygenate conversion effluent stream.

U.S. Pat. Nos. 6,403,854 and 6,459,009 to Miller et al. disclose a process for converting oxygenate to light olefins in which the reactor effluent is quenched with an aqueous stream in a two-stage process to facilitate the separation of hydrocarbon gases from any entrained catalyst fines, as well as to remove water and any heavy by-products such as $C_6+$ hydrocarbons. A portion of the waste water stream withdrawn from the bottom of the quench tower is recycled to the quench tower at a point above where the reactor effluent is introduced to the quench tower. The vapor product stream from the quench tower is compressed, passed to an adsorption zone for the selective removal of oxygenates and then passed to a caustic wash zone for removal of carbon dioxide. The resultant carbon dioxide free light olefin stream is passed to a dryer zone for the removal of water and passed to a conventional light olefin recovery zone.

U.S. Patent Application Publication No. 2003/0130555, published Jul. 10, 2003, discloses a process for separating oxygenated hydrocarbons from the olefin product of an oxygenate to conversion olefins reaction. The product is initially sent to a cooling unit, such as a quench tower, from which cooled olefin product is separated as an olefin vapor stream. The water containing bottoms stream can be recycled through a heat exchanger for cooling and/or removed from the cooling unit to a first separator, such as a distillation column, to provide an oxygenated hydrocarbon product of reduced water content and remaining water as a bottoms product. The olefin vapor stream is compressed to at least 30 psia (207 kPa), preferably 100 to 500 psia (689 to 3447 kPa), and directed to a second separator that provides an olefin vapor product and a liquid oxygenated hydrocarbon-containing stream. The liquid oxygenated hydrocarbon containing stream can then be combined with the water containing bottoms stream or directly added to the first separator to provide an oxygenated hydrocarbon product recovered from the first separator that is reduced in water content and can be used as fuel or co-feed for the oxygenate reaction process. Before or after the compression step, the olefin vapor can be washed with methanol and/or water at a temperature of 40 to 200° F. (4 to 93° C.), preferably 80 to 120° F. (27 to 49° C.).

All of the above references are incorporated herein by reference in their entirety.

SUMMARY

In one aspect, the invention relates to a process for producing olefins comprising:
  (a) providing a first vapor effluent stream from an oxygenate to olefin conversion reaction, said first vapor effluent stream comprising $C_2$ and $C_3$ olefins, $C_4$ hydrocarbons, and $C_2$ to $C_6$ carbonyl compounds;
  (b) adjusting the temperature and pressure of the first vapor effluent stream to produce a second vapor effluent stream having a pressure ranging from about 100 psig to about 350 psig (790 to 2514 kPa) and a temperature ranging from about 70° F. to about 120° F. (21 to 49° C.), said second vapor effluent stream containing about 50 wt. % or more of the $C_4$ hydrocarbons provided in the first vapor effluent stream;

(c) washing the second vapor effluent stream with a liquid alcohol-containing stream to produce a third vapor effluent stream; and (d) washing the third vapor effluent stream with water to provide a fourth vapor effluent stream, said fourth vapor effluent stream comprising about 1.0 wt. % or less $C_2$ to $C_6$ carbonyl compounds.

Conveniently, said adjusting (b) produces said second vapor effluent stream with a pressure ranging from about 120 psig to about 290 psig (928 to 2101 kPa), such as from about 140 psig to about 170 psig (1023 to 1273 kPa).

Conveniently, said adjusting (b) produces said second vapor effluent stream with a temperature ranging from about 80° F. to about 110° F. (27 to 43° C.), such as from about 90° F. to about 100° F. (32 to 38° C.).

Conveniently, said second vapor effluent stream contains at least 60 wt. %, such as at least 70 wt %, for example at least 80 wt %, such as at least 90 wt %, for example at least 95 wt %, of the $C_4$ hydrocarbons in the first vapor effluent stream.

Conveniently, the washing (c) is conducted at a temperature of at least 80° F. (27° C.), such as at least 90° F., and generally no more than 120° F. (49° C.), such as no more than 110° F. (43° C.), for example no more than 100° F. (38° C.).

Conveniently, the washing (c) is conducted at a pressure ranging from about 100 psig to about 350 psig (790 to 2514 kPa), such as 120 psig to about 290 psig (928 to 2101 kPa), for example from about 140 psig to about 170 psig (1023 to 1273 kPa).

Conveniently, the liquid alcohol-containing stream comprises methanol, ethanol or a mixture thereof and may optionally contain water. In one embodiment the alcohol is methanol and, in particular, methanol having a purity of at least 40 wt %, such as at least 75 wt %, for example at least 95 wt %, typically at least 99 wt %. Conveniently, the amount of methanol employed in the washing (c) is at least 0.03 lb, such as at least 0.05 lb, for example at least 0.07 lb methanol (as pure methanol) per lb of the second vapor effluent stream. In addition, the amount of methanol employed in the washing (c) is generally no more than 0.5 lb, such as no more than 0.2 lb, for example no more than 0.1 lb methanol (as pure methanol) per lb of the second vapor effluent stream.

Conveniently, the washing (d) is conducted at a temperature of at least 80° F. (27° C.), such as at least 90° F., and generally no more than 120° F. (49° C.), such as no more than 110° F. (43° C.), for example no more than 100° F. (38° C.).

Conveniently, the washing (d) is conducted at a pressure ranging from about 100 psig to about 350 psig (790 to 2514 kPa), such as 120 psig to about 290 psig (928 to 2101 kPa), for example from about 140 psig to about 170 psig (1023 to 1273 kPa).

Conveniently, said fourth vapor effluent stream comprises less than 0.5 wt. %, such as less than 0.1 wt %, for example less than 500 ppm wt, of $C_2$ to $C_6$ carbonyl compounds.

Conveniently, said fourth vapor effluent stream comprises less than 1.0 wt. %, such as less than 0.1 wt %, for example less than 500 ppm wt, of methanol.

In one embodiment, the process further comprises (e) removing acid gas from the fourth effluent stream.

In a further embodiment, the process further comprises (f) drying the fourth effluent stream such that the dried fourth effluent stream has a dew point no greater than −150° F. (−101° C.), such as no greater than −200° F. (−129° C.). Conveniently, the drying (f) is conducted after the removing acid gas (e).

In a yet further embodiment, the process also comprises fractionating the $C_3$ and $C_4$ containing hydrocarbons in the fourth vapor effluent stream to produce a $C_3$ containing stream and a first $C_4$ containing stream, wherein the first $C_4$ containing stream comprises less than 5 wt %, such as less than 1 wt %, for example less than 0.1 wt %, $C_3$ and lower hydrocarbons. Conveniently, said first $C_4$ containing stream comprises less than 5 wt %, such as less than 1 wt %, for example less than 5000 ppm wt, typically less than 500 ppm wt, of $C_2$ to $C_6$ carbonyl compounds.

Conveniently, said first vapor effluent stream in (a) and said first $C_4$ containing stream comprise $C_5+$ hydrocarbons and said first $C_4$ containing stream is subjected to a further fractionation to separate $C_5+$ hydrocarbons therefrom.

Conveniently, said first vapor effluent stream in (a) and said first $C_4$ containing stream comprise dimethyl ether and said first $C_4$ containing stream is subjected to further fractionation to remove dimethyl ether therefrom.

Conveniently, said adjusting in (b) separates a second liquid $C_4$ containing stream from said first vapor effluent stream and said second liquid $C_4$ containing stream is combined with said first $C_4$ containing stream to produce a third $C_4$ containing stream comprising less than 5 wt %, such as less than 1 wt %, for example less than 5000 ppm wt, typically less than 500 ppm wt, of $C_2$ to $C_6$ carbonyl compounds.

In a further aspect, the invention resides in a process for producing olefins comprising:

(a) contacting an oxygenate feed with a molecular sieve catalyst to produce a vapor product stream comprising $C_2$ and $C_3$ olefins, $C_4$ hydrocarbons, water and oxygenate compounds, including $C_2$ to $C_6$ carbonyl compounds;

(b) cooling said product stream to condense therefrom a liquid stream rich in water and oxygenate compounds and produce a first vapor effluent stream comprising $C_2$ and $C_3$ olefins, $C_4$ hydrocarbons, and $C_2$ to $C_6$ carbonyl compounds;

(c) compressing said first vapor effluent stream to produce a second vapor effluent stream having a pressure ranging from about 100 psig to about 350 psig (790 to 2514 kPa) and a temperature ranging from about 70° F. to about 120° F. (21 to 49° C.), said second vapor effluent stream containing about 50 wt. % or more of the $C_4$ hydrocarbons in the first vapor effluent stream;

(d) washing the second vapor effluent stream with a liquid methanol-containing stream to produce a third vapor effluent stream and an liquid oxygenate-containing methanol stream; and (e) washing the third vapor effluent stream with liquid water to produce a fourth vapor effluent stream and an oxygenate-containing water stream, said fourth vapor effluent stream comprising about 1.0 wt. % or less $C_2$ to $C_6$ carbonyl compounds.

Conveniently, said oxygenate feed comprises methanol and/or ethanol, and preferably methanol.

Conveniently, said compressing in (c) is conducted in a plurality of stages.

In one embodiment of the further aspect of the invention, at least a portion of said oxygenate-containing water stream, or said oxygenate-containing methanol stream, or the liquid stream rich in water from (b), or any combination thereof, is fractionated to produce an oxygenate-rich overhead stream and a water-rich liquid bottoms stream. Conveniently, at least a portion of said oxygenate-rich overhead stream is recycled as part of the oxygenate feed for said contacting in (a). Additionally, or as an alternative, at least a portion of the water-rich liquid bottoms stream is recycled as part of the liquid water used in the washing (e). Each of these three streams may be fractionated individually, or any and all may be fractionated in a single fractionation device, introduced in combination or with each stream being sent to a separate portion of the single fractionation device.

As used herein, the term "$C_x$ hydrocarbon" indicates aliphatic, olefin, diolefin, acetylene, or cyclic variations thereof, or in appropriate cases aromatic, hydrocarbon molecules having the number of carbon atoms represented by the subscript "x" Similarly, the term "$C_x$-containing stream" means the stream contains $C_x$ hydrocarbon. The more specific molecule is represented by a more explicit term in place of "hydrocarbon", so that, for example, "$C_4$ olefin" indicates butene-1, or butene-2, or isobutene, or combinations thereof. The term "$C_x+$ hydrocarbons" indicates those molecules noted above having the number of carbon atoms represented by the subscript "x" or greater. For example, "$C_4+$ hydrocarbons" would include $C_4$, $C_5$ and higher carbon number hydrocarbons. Similarly "$C_x-$ hydrocarbons" indicates those molecules noted above having the number of carbon atoms represented by the subscript "x" or fewer. As used herein, hydrocarbons do not contain an oxygen molecule and thus are not to be confused with the term oxygenate or its various more specific forms, such as alcohol, ether, aldehyde, ketone or carbonyl.

As used herein, the term $C_2$ to $C_6$ carbonyl compounds is defined as meaning one or more molecules containing from 2 to 6 carbon atoms that further comprise at least one oxygen atom in an aldehyde (oxygen that has a double bond to a carbon atom that in turn has a single bond to one other carbon atom and one hydrogen atom) or ketone (oxygen that has double bond to a carbon atom that in turn has a single bond to each of two other carbon atoms) moiety.

DETAILED DESCRIPTION OF THE EMBODIMENTS

Figure 1:
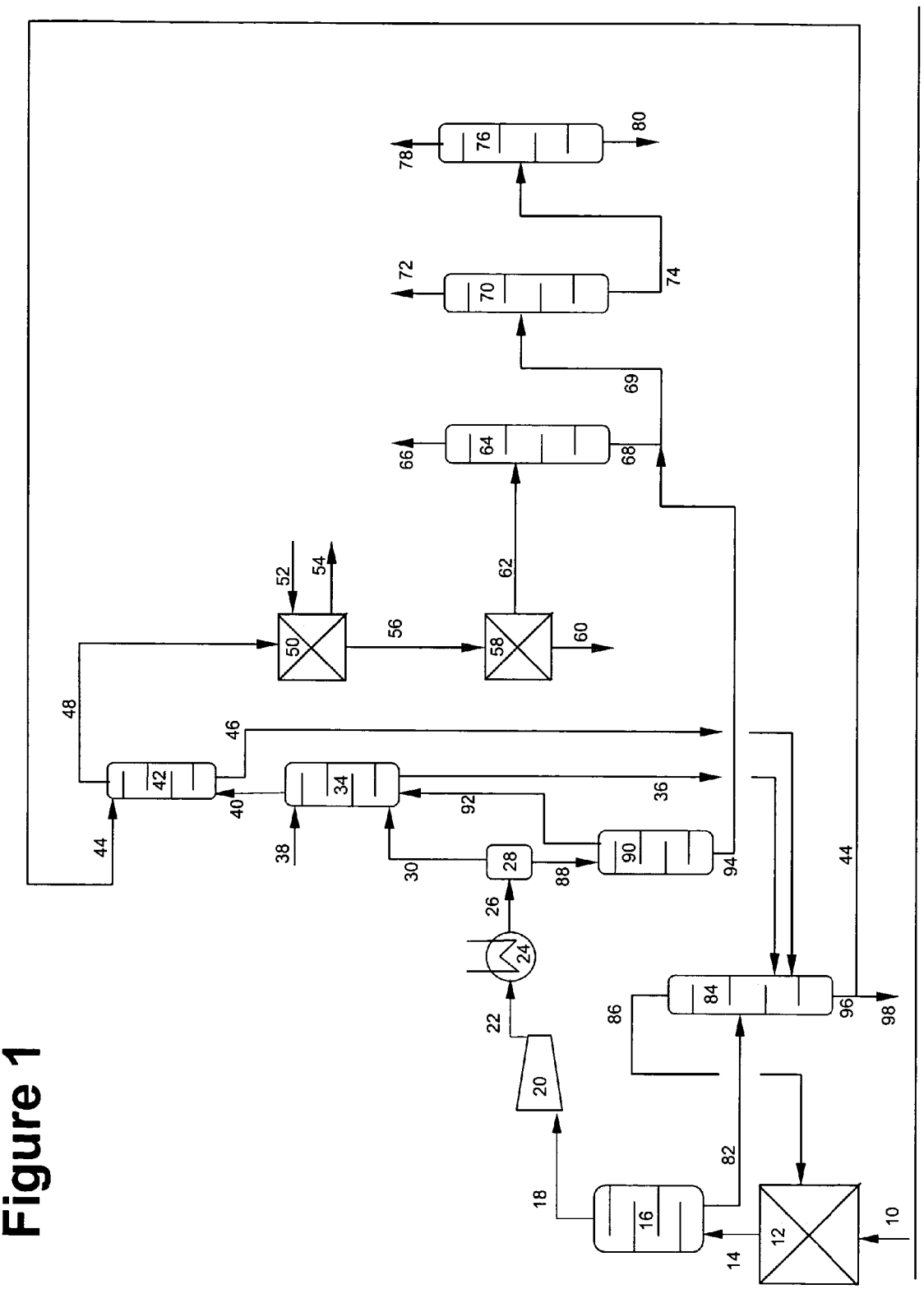
FIG. 1 is a schematic flow diagram illustrating a process for producing an olefins stream according to one example of the present invention.

Molecular Sieves and Catalysts Thereof for Use in OTO Conversion

Molecular sieves suited to use for converting oxygenates to olefins (OTO) have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types,* 5th edition, Elsevier, London, England (2001), which is herein fully incorporated by reference.

Non-limiting examples of these molecular sieves are the small pore molecular sieves of a framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves of a framework-type selected from the group consisting of AFO, AEL, EUO, HEU, FER, MEL, MFI, MTW, MTT, TON, and substituted forms thereof; and the large pore molecular sieves of a framework-type selected from the group consisting of EMT, FAU, and substituted forms thereof. Other molecular sieves have a framework-type selected from the group consisting of ANA, BEA, CFI, CLO, DON, GIS, LTL, MER, MOR, MWW and SOD. Non-limiting examples of the preferred molecular sieves, particularly for converting an oxygenate containing feedstock into olefin(s), include those having a framework-type selected from the group consisting of AEL, AFY, BEA, CHA, EDI, FAU, FER, GIS, LTA, LTL, MER, MFI, MOR, MTT, MWW, TAM and TON. In one embodiment, the molecular sieve used in the process of the invention has an AEI topology or a CHA topology, or a combination thereof, preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1-67, Elsevier Science, B. V., Amsterdam, Netherlands (2001).

The small, medium and large pore molecular sieves have from a 4-ring to a 12-ring or greater framework-type. In one embodiment, the molecular sieves used herein have 8-, 10- or 12-ring structures or larger and an average pore size in the range of from about 3 Å to 15 Å. More typically, the molecular sieves utilized in the invention, such as silicoaluminophosphate molecular sieves, have 8-rings and an average pore size less than about 5 Å, such as in the range of from 3 Å to about 5 Å, for example from 3 Å to about 4.5 Å, particularly from 3.5 Å to about 4.2 Å.

Molecular sieves used herein typically have two or more [$SiO_4$], [$AlO_4$] and/or [$PO_4$] tetrahedral units. These silicon, aluminum and/or phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851, 106 (CrAPO), U.S. Pat. Nos. 4,758,419, 4,882,038, 5,434, 326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), International Patent Publication No. WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves include aluminophosphate (ALPO) molecular sieves, silicoaluminophosphate (SAPO) molecular sieves and substituted, preferably metal substituted, forms thereof. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

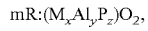

$$mR:(M_xAl_yP_z)O_2,$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanides of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. Patent Application Publication No. 2002/0165089 published Nov. 7, 2002 and International Patent Publication No. WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

The molecular sieves useful for oxygenates to olefins conversion processes are synthesized and then made or formulated into catalysts by combining the synthesized molecular sieves with a binder and/or a matrix material to form a molecular sieve catalyst composition. This molecular sieve catalyst composition is formed into useful shaped and sized particles by well-known techniques such as spray drying, pelletizing, extrusion, and the like.

Oxygenate to Olefins (OTO) Process

The feedstock to an oxygenate to olefins process comprises one or more oxygenates, more specifically, one or more organic compound(s) containing at least one oxygen atom. Typically, the oxygenate in the feedstock comprises one or more alcohol(s), generally aliphatic alcohol(s) where the aliphatic moiety of the alcohol(s) has from 1 to 20 carbon atoms, such as from 1 to 10 carbon atoms, and conveniently from 1 to 4 carbon atoms. The alcohols useful as feedstock in an oxygenate to olefins process include lower straight and branched chain aliphatic alcohols and their unsaturated counterparts.

Non-limiting examples of suitable oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. Typically, the feedstock is selected from one or more of methanol, ethanol, dimethyl ether and diethyl ether, especially methanol and dimethyl ether, and preferably methanol.

In addition to the oxygenate component, such as methanol, the feedstock may contains one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

In the OTO process, the various feedstocks discussed above, particularly a feedstock containing an alcohol, are converted over a molecular sieve catalyst, primarily into one or more olefin(s). The olefin(s) or olefin monomer(s) produced from the feedstock typically have from 2 to 30 carbon atoms, such as 2 to 8 carbon atoms, for example 2 to 6 carbon atoms, especially 2 to 4 carbons atoms, and preferably are ethylene and/or propylene.

The present process can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the present process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 $hr^{-1}$ to about 1000 $hr^{-1}$. In one embodiment, the WHSV is greater than 20 $hr^{-1}$ and, where feedstock contains methanol and/or dimethyl ether, is in the range of from about 20 $hr^{-1}$ to about 300 $hr^{-1}$.

Where the process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec.

The process of the invention is conveniently conducted as a fixed bed process, or more typically as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one practical embodiment, the process is conducted as a fluidized bed process or high velocity fluidized bed process utilizing a reactor system, a regeneration system and a recovery system.

In such a process the reactor system would conveniently include a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of liquid feedstock fed as a liquid and/or a vapor to the reactor system is in the range of from 0.1 weight percent to about 85 weight percent, such as from about 1 weight percent to about 75 weight percent, more typically from about 5 weight percent to about 65 weight percent based on the total weight of the feedstock including any diluent contained therein. The liquid and vapor feedstocks may be the same composition, or may contain varying proportions of the same or different feedstocks with the same or different diluents.

The feedstock entering the reactor system is preferably converted, partially or fully, in the first reactor zone into a vapor product stream that enters the disengaging vessel along with the coked catalyst composition. In the preferred embodiment, cyclone(s) are provided within the disengaging vessel to separate the coked catalyst composition from the vapor product stream containing one or more olefin(s) within the disengaging vessel. Although cyclones are preferred, gravity effects within the disengaging vessel can also be used to separate the catalyst composition from the vapor product stream. Other methods for separating the catalyst composition from the vapor product stream include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172 kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes, and the volume of oxygen in the regeneration gas may be in the range of from about 0.01 mole percent to about 5 mole percent based on the total volume of the gas.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are disclosed in U.S. Pat. No. 6,290,916 (controlling moisture), which is herein fully incorporated by reference.

The regenerated catalyst composition withdrawn from the regeneration system, preferably from a catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Fluidized Beds*, Grace, Avidan and Knowlton, eds., Blackie, 1997 (336-337), which is herein incorporated by reference.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The vapor product stream is withdrawn from the disengaging system and passed to a recovery system for separating and purifying the olefins and other useful components in the product stream.

OTO Product Recovery Process

The vapor product stream from the oxygenate to olefin conversion process described above is a complex mixture comprising the desired $C_2$ to $C_4$ olefins, unconverted oxygenates, by-product oxygenates (including $C_2$ to $C_6$ aldehydes and ketones), heavier hydrocarbons (including aromatics) and large amounts of water.

On leaving the OTO reactor system, the vapor product stream is at reaction temperature and pressure and hence is initially cooled, typically in a quench tower employing water as the quench medium. In the quench tower, most of the water (generally at least 90 wt %) in the product stream is condensed and is removed from the bottom of the tower as a liquid water-rich bottoms stream. The light hydrocarbons and light oxygenates in the product stream are removed from the top of the quench tower as a first vapor effluent stream at a first pressure.

The water-rich bottoms stream from the quench tower will contain various other materials in addition to water, such as unreacted oxygenate feedstock, e.g., methanol, and other oxygenates created as byproducts of the oxygenate to olefins reaction, for example, but not limited to, ethanol, ethanal, propanal, acetone, butanone, dimethyl ether, methyl ethyl ether, acetic acid and propionic acid. The proportions of these oxygenates in the water-rich bottoms stream may vary widely dependent upon the nature of the oxygenate to olefin reactor, including feedstock, catalyst, WHSV, temperature and pressure. Further, the proportions of these oxygenates in the water-rich bottoms stream may vary widely dependent upon the specifics of the quench tower, such as the pressure, temperature and height of the tower and nature of the tower internals.

Regardless of the exact composition, the water-rich bottoms stream will need to undergo further processing to provide components in an appropriate state for use or further treatment, e.g., provide a water stream low enough in organic content for typical water waste treatment, or provide an oxygenate stream low enough in water content for use as fuel or for addition to some point in the oxygenate to olefins process or apparatus. Examples of such treatment can be found in U.S. Pat. Nos. 6,121,504, 6,403,854 and 6,459,009 and U.S. patent application Ser. No. 10/720,505 filed Nov. 24, 2003.

In one embodiment, the water-rich bottoms stream is directed to a water-oxygenate fractionation tower, e.g., a water-methanol fractionation tower, which is operated to separate methanol and other oxygenates as an overhead, e.g., greater than about 20 wt % oxygenates (with the balance being largely water), and substantially pure water as a bottoms stream, typically, greater than about 90 wt % water, say, greater than about 95 wt % water, e.g., greater than about 99 wt % water. The oxygenate-rich overhead product of the fractionation tower can be used for various purposes, including as a feedstock to the OTO reactor along with the primary oxygenate feedstock. If the oxygenate-rich overhead product is taken as a vapor, this provides vaporized methanol/oxygenate feed to the reactor with virtually no incremental heat input beyond that already required in the reboiler of the methanol-water fractionation tower, with no incremental heat load in the primary feed vaporization section of the OTO reactor.

The first vapor effluent stream exiting as overhead from the quench tower is typically at a first pressure of from about 1 psig to about 100 psig (108 to 790 kPa), such as from about 5 psig to about 80 psig (135 to 653 kPa), for example from about 10 psig to about 30 psig (170 to 308 kPa). Conveniently, the temperature of the first vapor effluent stream is at least 80° F. (27° C.) and generally no more than 120° F. (49° C.), such as no more than 110° F. (43° C.), for example no more than 100° F. (38° C.). The first vapor effluent stream normally comprises from about 0.5 to about 5 wt %, such as from about 1 to about 4 wt %, of $C_2$ to $C_6$ carbonyl compounds and no more than 10 wt %, for example no more than 5 wt %, such as no more than 2 wt %, water.

After exiting the quench tower, the first vapor effluent stream is compressed and cooled, conveniently using multiple stages of compression and cooling, to produce a second vapor effluent stream. In one embodiment, the compression and cooling of the first vapor effluent stream causes partial condensation so as to produce a second effluent liquid stream in addition to the second vapor effluent stream. The second vapor effluent stream contains the lighter components, including the desired olefins, from the first effluent stream, and in particular normally contains at least 50 wt. %, such as at least 60 wt %, for example at least 70 wt %, such as at least 80 wt %, for example at least 90 wt %, such as at least 95 wt %, of the $C_4$ hydrocarbons in the first vapor effluent stream. The second effluent liquid stream contains the heavier components, including some oxygenates, as well as the remaining $C_4$ hydrocarbons from the first vapor effluent stream, and further contains some $C_3$ and lighter components. The second effluent liquid stream can be recycled to the quench tower or back to the OTO reactor, typically by way of an water-oxygenate fractionation tower, among other dispositions, as will be discussed below.

Where the compression and cooling of the first vapor effluent stream to produce the second vapor effluent stream occurs in a plurality of stages, partial condensation and removal of a liquid fractions from the first vapor effluent stream conveniently occurs at each compression stage, conveniently in a knock-out drum provided after each compression/cooling stage. The resultant liquid fractions, including but not limited to the second effluent liquid stream, will have varying compositions dependent on the composition of the first vapor effluent stream, and the pressures and temperatures at which the partial condensation is effected, and they can be recycled independently or in combination to the quench tower or OTO reactor or methanol-water fractionation tower.

The second vapor effluent stream exiting the compression/cooling stage or stages is at a second pressure greater than the first pressure. Conveniently, the second pressure is less than 350 psig (2514 kPa), such as less than 200 psig (1480 kPa), for example less than 170 psig (1273 kPa), and greater than 100 psig (790 kPa), such as greater than 140 psig (1066 kPa). Conveniently, said second vapor effluent stream is at a temperature of at least 70° F. (21° C.), for example at least 80° F. (27° C.), such as at least 90° F., and generally no more than 120° F. (49° C.), such as no more than 110° F. (43° C.), for example no more than 100° F. (38° C.).

The second vapor effluent stream is then subjected to a first washing step in which the second vapor effluent stream is washed with a liquid alcohol-containing stream in a first vapor-liquid contacting device at a third pressure not greater than the second pressure. Conveniently, the third pressure is less than 350 psig (2514 kPa), such as less than 200 psig (1480 kPa), for example less than 170 psig (1273 kPa), and greater than 100 psig (790 kPa), such as greater than 140 psig (1066 kPa). The first washing step serves to remove aldehydes and ketones from the second vapor effluent vapor stream and produces a third vapor effluent stream, containing the desired olefin product, and a liquid oxygenate-containing alcohol stream. Conveniently, said third vapor effluent stream comprises less than 0.5 wt. %, such as less than 0.1 wt %, for example less than 500 ppm wt, of $C_2$ to $C_6$ carbonyl compounds.

Conveniently, said liquid alcohol-containing stream used in the first washing step comprises methanol and/or ethanol, and preferably methanol, and thus is a liquid methanol-containing stream. The methanol employed as a liquid methanol-containing stream can contain water and traces (such as less than 2 wt %, or less than 1 wt %, or less than 0.5 wt % or less than 0.1 wt %) of other alcohols and hydrocarbons. In general, methanol is more effective than water and other alcohols in removing such carbonyl species from hydrocarbons in a vapor-liquid wash. Typically, therefore, the alcohol-containing liquid stream used in the first washing step comprises at least 40 wt % methanol and less than 60 wt % water, such as at least 75 wt % methanol and less than 25 wt % water, for example at least 90 wt % methanol and less than 10 wt % water, or such as at least 99 wt % methanol and less than 1 wt % water.

In general, the temperature employed in the first washing step should be no more than 120° F. (49° C.) so as to enhance the oxygenate adsorption capacity of the alcohol, especially methanol, and limit the amount of vaporized alcohol exiting the first vapor-liquid contacting device with the third effluent stream. In addition, the temperature employed in the first washing step is generally at least 70° F. (21° C.) so as to limit the amount of hydrocarbons adsorbed by the alcohol to acceptable levels. Conveniently, the temperature of the first washing step is at least 80° F. (27° C.), such as at least 90° F., and no more than 110° F. (43° C.), for example no more than 100° F. (38° C.).

Conveniently, where the alcohol utilized is methanol, the amount of methanol employed in the first washing step is at least 0.03 lb (as pure methanol) per lb of the second vapor effluent stream so as to ensure that there is sufficient methanol to (1) achieve the required low level of oxygenate in the $C_4$ component of third vapor effluent stream and (2) prevent the formation of a third, aqueous liquid phase in the first vapor-liquid contacting device. In addition, the amount of methanol employed in the first washing step is generally no more than 0.5 lb (as pure methanol) per lb of the second vapor effluent stream so as to limit the amount of prime olefin (ethylene and propylene) removed into the liquid oxygenate-containing methanol stream. Preferably, the amount of methanol employed is as at least 0.05 lb, such as at least 0.06 lb, for example at least 0.07 lb methanol (as pure methanol) per lb of the second vapor effluent stream. In addition, the amount of methanol employed is preferably no more than 0.2 lb, such as no more than 0.15 lb, for example no more than 0.1 lb methanol (as pure methanol) per lb of the second vapor effluent stream.

In one embodiment, the first vapor-liquid contacting device is a countercurrent fractional distillation tower, in which the second vapor effluent stream is directed into the bottom of the tower and methanol is directed into the top of the tower. The third vapor effluent stream exits the tower as overhead while the liquid oxygenate-containing methanol stream exits as a bottoms stream.

The third vapor effluent stream is then subjected to a second washing step in which the third vapor effluent vapor stream is washed with water in a second vapor-liquid contacting device, again typically a countercurrent fractional distillation tower, to produce a water-washed fourth vapor effluent stream as an overhead product and an liquid oxygenate-containing water stream as a bottoms product. Conveniently, the liquid water employed in the second washing step is the substantially pure water bottoms stream obtained from the water-oxygenate fractionation tower.

In general, the temperature employed in the second washing step should be no more than 120° F. (49° C.) so as to enhance the oxygenate adsorption capacity of the water and limit the amount of water vapor exiting the second vapor-liquid contacting device with the fourth vapor effluent stream. Conveniently, the temperature of the second washing step is at least 70° F. (21° C.), for example at least 80° F. (27° C.), such as at least 90° F., and no more than 110° F. (43° C.), for example no more than 100° F. (38° C.). Conveniently, the second washing step is conducted at a pressure in the same ranges as noted earlier for the third pressure, and in a specific embodiment slightly below (say about 5 to about 20 psi below) said third pressure.

Conveniently, said fourth vapor effluent stream comprises less than 0.5 wt. %, such as less than 0.1 wt %, for example less than 500 ppm wt, of $C_2$ to $C_6$ carbonyl compounds. In addition, the fourth vapor effluent stream conveniently comprises less than 1.0 wt. %, such as less than 0.1 wt %, for example less than 500 ppm wt, of methanol. The fourth vapor effluent stream can then be processed to recover the $C_2$ to $C_4$ olefins and higher hydrocarbons present in this stream.

In one embodiment of such a recovery process, at least part of the fourth vapor effluent stream is contacted with a basic component, such as caustic or an amine, to remove the bulk of the carbon dioxide therefrom (thus removing "acid gas" from the fourth vapor effluent stream), whereafter the $CO_2$-depleted stream is dried, for example in a molecular sieve drier, so that the dried fourth effluent stream has a dew point no greater than −150° F. (−101° C.), such as no greater than −200° F. (−129° C.).

In another embodiment of such a recovery process, at least part of the $C_3$ and $C_4$ hydrocarbons contained in the fourth vapor effluent stream, or in the dried fourth effluent stream, is separated to produce a $C_3$ containing stream and a first $C_4$ containing stream. This separation is effected, for example, in a fractional distillation tower, wherein the $C_3$ containing stream is taken as an overhead product and the first $C_4$ containing stream is taken as a bottoms product. This separation may be conducted either before or after separating $C_2$− hydrocarbons from the fourth vapor effluent stream, and the $C_3$ and $C_2$− hydrocarbons can be further processed to produce high purity, e.g., 95 wt. % or greater, such as 99 wt. % or greater, ethylene and propylene, in other separation steps such as fractional distillation columns.

The composition of the first $C_4$ containing stream can vary widely, depending, for example, on the sequence of separation steps to which the fourth vapor effluent stream or dried fourth effluent stream is conducted, e.g., the order in which fractional distillation of various components is conducted. In one embodiment, the first vapor effluent stream comprises $C_5$+ hydrocarbons, and at least part of the $C_3$ and $C_4$ hydrocarbons contained in the fourth vapor effluent stream, or in the dried fourth effluent stream, is separated to produce a $C_3$ containing stream and a first $C_4$ containing stream prior to separation of $C_4$ hydrocarbons from $C_5$+ hydrocarbons. In this embodiment, the separation is conducted such that there is a low amount of dimethyl ether in the first $C_4$ containing stream, generally 1 wt. % or less, such as 0.5 wt. % or less, or 0.1 wt. % or less, or even 500 wppm or less.

In this embodiment, the first $C_4$ containing stream comprises at least 40wt %, such as at least 50 wt %, such as at least 60 wt % of $C_4$ hydrocarbons, including $C_4$ olefins, and at least 10 wt %, such as at least 15 wt %, for example at least 20 wt %, of $C_5$ hydrocarbons, including $C_5$ olefins, and varying amounts of $C_6$ and higher hydrocarbons. Typically the first $C_4$ containing stream comprises less than 5 wt %, such as less than 1 wt %, for example less than 0.1 wt % $C_3$ and lower hydrocarbons and no more than 5 wt %, such as no more than 2 wt %, such as no more than 1 wt %, such as no more than 5000 ppm wt, such as no more than 1000 ppm wt, such as no more than 500 ppm wt, for example no more than 250 ppm wt, of $C_2$ to $C_6$ carbonyl compounds. The first $C_4$ containing stream can be extracted directly as a product stream for use as a fuel gas or as a feed for processes, such as, hydrogenation (for example, to convert butadiene to butenes and butane), alkylation (for example, to produce higher saturated hydrocarbons), and oligomerization (for example, to produce higher olefins). Alternatively, the first $C_4$ containing stream can undergo further separation into its individual components.

In one embodiment, the first $C_4$ containing stream is passed to a further fractionator to remove $C_5$+ hydrocarbons and produce a $C_4$ hydrocarbon product stream containing 80 wt % or greater $C_4$ hydrocarbons, such as 90 wt. % or greater $C_4$ hydrocarbons, or 98% or greater $C_4$ hydrocarbons, and less than 5 wt %, such as less than 1 wt %, for example less than 5000 ppm wt, typically less than 500 ppm wt, of $C_2$ to $C_6$ carbonyl compounds. The $C_4$ hydrocarbon product stream can be used in the same applications outlined above for the first $C_4$ containing stream and in addition can be used in the manufacture of butene-1, methyl ethyl ketone, and methyl tertiary butyl ether, among other uses.

In another embodiment, the first vapor effluent stream comprises dimethyl ether, and at least part of the $C_3$ and $C_4$ hydrocarbons contained in the fourth vapor effluent stream, or in the dried fourth effluent stream, is separated to produce a $C_3$ containing stream and a first $C_4$ and DME containing stream prior to separation of $C_4$ hydrocarbons from dimethyl ether. The first $C_4$ and DME containing stream conveniently comprises 50 wt % or greater $C_4$ hydrocarbons, such as 60 wt. % or greater $C_4$ hydrocarbons, or 70% or greater $C_4$ hydrocarbons; from 1 wt. % to 30 wt. % DME, such as from 5 wt. % to 25 wt. % DME;, and 5 wt % or less, such as 1 wt % or less, for example 5000 wppm or less, or 500 wppm or less of $C_2$ to $C_6$ carbonyl compounds.

The first $C_4$ and DME containing stream is then subjected to an additional fractionation step to remove dimethyl ether. The separation of dimethyl ether can be conducted either before or after the fractionation to separate the $C_4$ and $C_5$+ hydrocarbons. The dimethyl ether so generated can be used as a fuel or can be recycled to the OTO reaction. The $C_4$+ hydrocarbon stream resulting from the separation of DME from the first $C_4$ and DME containing stream is also considered a first $C_4$ containing stream, characterized above. Additionally, the $C_4$ hydrocarbon stream resulting from the separation of dimethyl ether and C5+ hydrocarbons from the first $C_4$ and DME containing stream is also considered a $C_4$ hydrocarbon product stream, characterized above.

In a modification of the process described above, the second effluent liquid stream is subjected to further processing to separate $C_3$ and lighter components from $C_4$ and heavier components. Conveniently this separation can occur in a stripper tower, wherein the second effluent liquid is provided to the top of a staged distillation tower having a reboiler but no condensor. This separation will create a second $C_4$ containing stream, for example as the liquid bottoms product of a stripper tower, that has very little $C_3$ and lighter components, for example 5.0 wt. % or less, or 1.0 wt. % or less, or 0.1 wt. % or less. Further, a fifth vapor effluent stream will be produced, for example as the overhead product of the stripper tower, whose composition may vary widely depending upon the type of separation process employed and the conditions at which the separation is conducted. The fifth vapor effluent stream can, for example, comprise a considerable portion of the $C_4$ molecules in the second effluent liquid, say 10 wt. % or greater, or 20 wt. % or greater of the C4 molecules in the second effluent liquid.

Conveniently, at least a portion of the fifth vapor effluent stream is also provided to the first washing step along with the second vapor effluent stream, each stream being provided individually or in combination, to produce the third vapor effluent stream. In such an embodiment, the combined second vapor effluent stream and fifth vapor effluent stream (or portion thereof) provided to the first washing step contains at least 50 wt. %, such as at least 60 wt %, for example at least 70 wt %, such as at least 80 wt %, for example at least 90 wt %, such as at least 95 wt %, of the $C_4$ hydrocarbons in the first vapor effluent stream. Conveniently, the fifth vapor effluent stream, or alternatively the combined second vapor effluent and fifth vapor effluent stream, has the same ranges of temperature and pressure noted earlier for the second vapor effluent stream.

In addition, part or all of the first $C_4$ containing stream and the second $C_4$ containing stream can be combined to create a third $C_4$ containing stream, or in one embodiment at third $C_4$ and DME containing stream. The third $C_4$ containing stream, and the third $C_4$ and DME containing stream, conveniently have the attributes listed above for the first $C_4$ containing stream and the first $C_4$ and DME containing stream, respectively, and can be used in the same manner and subjected to the same process steps noted above for the first $C_4$ containing stream, for example to produce a $C_4$ hydrocarbon product stream, or for the first $C_4$ and DME containing stream, for example for use as a fuel or as a feed after a subsequent fractionation step.

Referring to FIG. 1, there is illustrated therein a process for converting methanol to olefins, particularly $C_2$ to $C_4$ olefins, according to one example of the invention. In this example, methanol is fed through line 10 to an oxygenate-to-olefins reactor 12 containing a molecular sieve catalyst which converts the methanol to a vapor product stream containing the desired olefins, unconverted methanol, by-product oxygenates (including $C_2$ to $C_6$ aldehydes and ketones), heavier hydrocarbons (including aromatics) and water.

The product stream exits the reactor 12 through line 14 and is fed to a quench tower 16, where the product stream is quenched with water to condense from the product stream a water-rich bottoms stream which exits the tower 16 through line 82 and is fed to a water-oxygenate fractionation tower 84. The overhead from the tower 16 is a first vapor effluent stream, which contains the desired olefin products and is fed through line 18 to a compressor 20. The compressor 20 compresses the first vapor effluent stream from a first pressure to a second, higher pressure and the resultant first compressed vapor effluent stream is fed through line 22 to an indirect heat exchanger 24.

The heat exchanger 24 cools the first compressed vapor effluent stream and the resultant first compressed and cooled vapor effluent stream is then fed by line 26 to a flash drum 28. In the flash drum 28, the first compressed and cooled vapor effluent stream is separated into a second vapor effluent stream, which exits the drum 28 through overhead line 30, and a second liquid effluent stream, which exits the drum 28 through bottoms line 88.

The second vapor effluent stream contains the desired olefin products and is fed by line 30 to the bottom of a first countercurrent fractional distillation column 34 while a liquid alcohol-containing stream, preferably a methanol-containing stream, is introduced into the top of the column 34 through line 38. The alcohol-containing stream removes $C_2$ to $C_6$ carbonyl compounds from the second vapor effluent stream as it flows upwards through the column 34 so that a liquid oxygenate-containing alcohol stream exits the bottom of the column 34 through line 36 and an alcohol-washed third vapor effluent stream exits the top of the column 34 through line 40. The line 40 feeds the third vapor effluent stream to the bottom of a second countercurrent fractional distillation column 42, while the line 36 feeds the oxygenate-containing alcohol stream to the water-oxygenate fractionation tower 84.

Water is introduced into the top of the column 42 through line 44 to remove the alcohol first wash medium and additional $C_2$ to $C_6$ carbonyl compounds from the third vapor effluent stream as it flows upwards through the column 42. As a result a liquid oxygenate-containing water stream exits the bottom of the column 42 through line 46 and a water-washed fourth vapor effluent stream exits the top of the column 42 through line 48. The oxygenate-containing water stream is then fed by line 46 to the water-oxygenate fractionation tower 84, while the fourth vapor effluent stream is fed by line 48 to a caustic tower 50.

Fresh caustic solution is introduced into the caustic tower 50 through line 52 to remove carbon dioxide from the fourth vapor effluent stream, while spent caustic solution is removed from the tower 50 through line 54. A $CO_2$-depleted fourth vapor effluent stream exits the tower 50 through line 56 and is passed to a molecular sieve adsorber 58, where water is removed from the fourth vapor effluent stream and, after desorption, is extracted through line 60.

A dried fourth vapor effluent stream exits the adsorber 58 through line 62 and is fed to a $C_3$- fractionation tower 64 where propylene and lighter hydrocarbons are removed as overhead through line 66 for further processing and a first $C_4$ and DME-containing stream is removed as bottoms through line 68. The first $C_4$ and DME-containing stream is then fed to a DME fractionation tower 70 which removes dimethyl ether as an overhead stream through line 72 for use as a fuel or for recycle to the reactor 12. The $C_4$+ bottoms stream in line 74 from the fractionation tower 70 is then fed to a $C_4$+ fractionation tower 76 which separates the $C_4$+ stream 74 into a $C_4$ overhead stream through line 78 low in $C_2$ to $C_6$ carbonyl compounds, and a $C_5$+ bottoms stream through line 80 which is also low in $C_2$ to $C_6$ carbonyl compounds.

In the embodiment shown in FIG. 1, the second liquid effluent stream exiting the flash drum 28 through line 88 is fed to a stripper 90 for separation into a second $C_4$ containing stream and a fifth vapor effluent stream. This separation ensures that most of the $C_3$ and lighter components in the second liquid effluent stream exit as overhead in the fifth vapor effluent stream, which is then fed by line 92 to the first countercurrent fractional distillation column 34 for alcohol washing. The second $C_4$ containing stream exits the stripper 90 as a liquid bottoms stream in line 94 and is passed together with the first $C_4$ and DME-containing stream in line 68 to the DME fractionation tower 70.

The water-oxygenate fractionation tower 84 receives the oxygenate-containing alcohol stream in line 36 from the first countercurrent fractional distillation column 34 and the oxygenate-containing water stream in line 46 from the second countercurrent fractional distillation column 42. The tower 84 is operated to separate these streams into an oxygenate-rich overhead stream in line 86, which is recycled to the reactor 12, and a water bottoms stream in line 96, which is partially recycled to the second countercurrent fractional distillation column 42 through line 44 and is partially purged through line 98.

The invention will now be more particularly described with reference to the following practical example of the process shown in FIG. 1.

EXAMPLE

A pilot plant trial of the process shown in FIG. 1 was conducted in which the second effluent stream was washed in the fractional distillation tower 28 at a pressure of 150 psig (1135 kPa) and a methanol flow rate of 15 lb/hour. The composition of the second effluent stream and the methanol-washed third effluent stream are shown below in Table 1.

TABLE 1

| Component | Second Effluent Stream (wt %) | Third Effluent Stream (wt %) | % Change |
|---|---|---|---|
| Dimethyl ether | 3.7661 | 2.7718 | −26.4015 |
| Methyl ethyl ether | 0.0101 | 0.0000 | −100.0000 |
| Methyl isopropyl ether | 0.0007 | 0.0000 | −100.0000 |
| Acetaldehyde | 0.0417 | 0.0378 | −9.5362 |
| 2-Methoxy butane | 0.0002 | 0.0000 | −100.0000 |
| Propanal | 0.0111 | 0.0000 | −100.0000 |
| Acrolein | 0.0001 | 0.0000 | −100.0000 |
| Methacrolein | 0.0036 | 0.0000 | −100.0000 |
| Unknown | 0.0003 | 0.0000 | −100.0000 |
| Butanal | 0.0032 | 0.0000 | −100.0000 |
| Methyl acetate | 0.0002 | 0.0000 | −100.0000 |
| Methanol | 2.7353 | 2.3179 | −15.2629 |
| Acetone | 0.1601 | 0.0813 | −49.2466 |
| Isovaleraldehyde | 0.0003 | 0.0000 | −100.0000 |
| Dimethylacetal | 0.0020 | 0.0000 | −100.0000 |
| Pentanal | 0.0005 | 0.0000 | −100.0000 |
| 2-Butanone | 0.0375 | 0.0000 | −100.0000 |
| Ethanol | 0.0008 | 0.0000 | −100.0000 |
| 3-Methyl-3-buten-2-one | 0.0014 | 0.0000 | −100.0000 |
| Unknown | 0.0002 | 0.0000 | −100.0000 |
| Crotonaldehyde | 0.0002 | 0.0000 | −100.0000 |
| 3-Methyl-2-butanone | 0.0042 | 0.0000 | −100.0000 |
| 3-Pentanone | 0.0021 | 0.0000 | −100.0000 |
| 2-Methyl butanol | 0.0002 | 0.0000 | −100.0000 |
| 2-Pentanone | 0.0022 | 0.0000 | −100.0000 |
| 3-Butenol | 0.0003 | 0.0000 | −100.0000 |
| 3-Methyl-2-pentanone | 0.0003 | 0.0514 | 19009.5609 |
| t-Butanol | 0.0001 | 0.0000 | −100.0000 |
| Methane | 1.2653 | 1.2563 | 0.0000 |
| Ethane | 0.5437 | 0.5308 | −2.3655 |
| Ethylene | 30.6933 | 29.9435 | −2.4430 |
| Propane | 0.9249 | 0.7663 | −17.1554 |
| Cyclopropane | 0.0031 | 0.0000 | −100.0000 |
| Propylene | 35.4988 | 31.0685 | −12.4804 |
| Isobutane | 0.0849 | 0.0587 | −30.8560 |
| n-Butane | 0.2579 | 0.1672 | −35.1748 |
| Methyl cyclopropane | 0.0039 | 0.0000 | −100.0000 |
| Trans-2-Butene | 5.1322 | 3.6158 | −29.5467 |
| 1-Butene | 3.3856 | 2.5235 | −25.4634 |
| Iso-Butene | 0.7129 | 0.5469 | −23.2929 |
| Cis-2-Butene | 3.8081 | 2.6364 | −30.7689 |
| Isopentane | 0.0043 | 0.0349 | 706.3496 |
| 1,2-Butadiene | 0.0561 | 0.0000 | −100.0000 |
| Pentane | 0.0581 | 0.0000 | −100.0000 |
| Methyl acetylene | 0.0022 | 0.0000 | −100.0000 |
| 1.3-Butadiene | 0.4457 | 0.0280 | −93.7131 |
| C5+ | 10.3408 | 4.0294 | −61.0339 |
| H2O/CO/CO2 | 0.0000 | 0.1403 | Undefined |

It will be seen from Table 1 that the methanol wash removes all the oxygenates in the first second effluent stream, except for part of the dimethyl ether, acetaldehyde, acetone and 3-methyl-pentanone.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A process for producing an olefins stream comprising:
    (a) providing a first vapor effluent stream from an oxygenate to olefin conversion reaction, said first vapor effluent stream comprising $C_2$ and $C_3$ olefins, $C_4$ hydrocarbons, and $C_2$ to $C_6$ carbonyl compounds;
    (b) adjusting the temperature and pressure of the first vapor effluent stream to produce a second vapor effluent stream having a pressure ranging from about 100 psig to about 350 psig (790 to 2514 kPa) and a temperature ranging from about 700° F. to about 120° F. (21 to 49° C.), said second vapor effluent stream containing about 50 wt. % or more of the $C_4$ hydrocarbons in the first vapor effluent stream;
    (c) washing the second vapor effluent stream with a liquid alcohol-containing stream to produce a third vapor effluent stream; and
    (d) washing the third vapor effluent stream with liquid water to provide a fourth vapor effluent stream, said fourth vapor effluent stream comprising about 1.0 wt. % or less $C_2$ to $C_6$ carbonyl compounds.

2. The process of claim 1 wherein said adjusting (b) produces said second vapor effluent stream with a pressure ranging from about 120 psig to about 290 psig (928 to 2101 kPa).

3. The process of claim 1 wherein said adjusting (b) produces said second vapor effluent stream with a pressure ranging from about 140 psig to about 170 psig (1023 to 1273 kPa).

4. The process of claim 1 wherein said adjusting (b) produces said second vapor effluent stream with a temperature ranging from about 80° F. to about 110° F. (27 to 43° C.).

5. The process of claim 1 wherein said adjusting (b) produces said second vapor effluent stream with a temperature ranging from about 90° F. to about 100° F. (32 to 38° C.).

6. The process of claim 1 wherein said second vapor effluent stream contains at least 60 wt. % of the $C_4$ hydrocarbons in the first vapor effluent stream.

7. The process of claim 1 wherein said second vapor effluent stream contains at least 70 wt % of the $C_4$ hydrocarbons in the first vapor effluent stream.

8. The process of claim 1 wherein said second vapor effluent stream contains at least 80 wt % of the $C_4$ hydrocarbons in the first vapor effluent stream.

9. The process of claim 1 wherein said second vapor effluent stream contains at least 90 wt % of the $C_4$ hydrocarbons in the first vapor effluent stream.

10. The process of claim 1 wherein said second vapor effluent stream contains at least 95 wt % of the $C_4$ hydrocarbons provided in the first vapor effluent stream.

11. The process of claim 1 wherein the washing (c) is conducted at a temperature of at least 80° F. (27° C.).

12. The process of claim 1 wherein the washing (c) is conducted at a temperature of at least 90° F. (32° C.).

13. The process of claim 1 wherein the washing (c) is conducted at a temperature of no more than 120° F. (49° C.).

14. The process of claim 1 wherein the washing (c) is conducted at a temperature of no more than 110° F. (43° C.).

15. The process of claim 1 wherein the washing (c) is conducted at a temperature of no more than 100° F. (38° C.).

16. The process of claim 1 wherein the washing (c) is conducted at a pressure of from about 100 psig to about 350 psig (790 to 2514 kPa).

17. The process of claim 1 wherein the washing (c) is conducted at a pressure of from about 120 psig to about 290 psig (928 to 2101 kPa).

18. The process of claim 1 wherein the washing (c) is conducted at a pressure of from about 140 psig to about 170 psig (1023 to 1273 kPa).

19. The process of claim 1 wherein the liquid alcohol-containing stream comprises methanol, or ethanol, or methanol and water, or ethanol and water, or methanol and ethanol and water.

20. The process of claim 1 wherein the liquid alcohol-containing stream comprises methanol.

21. The process of claim 20 wherein the methanol has a purity of at least 40 wt %.

22. The process of claim 20 wherein the methanol has a purity of at least 75 wt %.

23. The process of claim 20 wherein the methanol has a purity of at least 95 wt %.

24. The process of claim 20 wherein the methanol has a purity of at least 99 wt %.

25. The process of claim 20 wherein the amount of methanol employed in the washing (c) is at least 0.03 lb methanol (as pure methanol) per lb of the second vapor effluent stream.

26. The process of claim 20 wherein the amount of methanol employed in the washing (c) is at least 0.05 lb methanol (as pure methanol) per lb of the second vapor effluent stream.

27. The process of claim 20 wherein the amount of methanol employed in the washing (c) is at least 0.07 lb methanol (as pure methanol) per lb of the second vapor effluent stream.

28. The process of claim 20 wherein the amount of methanol employed in the washing (c) is no more than 0.5 lb methanol (as pure methanol) per lb of the second vapor effluent stream.

29. The process of claim 20 wherein the amount of methanol employed in the washing (c) is no more than 0.2 lb methanol (as pure methanol) per lb of the second vapor effluent stream.

30. The process of claim 20 wherein the amount of methanol employed in the washing (c) is no more than 0.1 lb methanol (as pure methanol) per lb of the second vapor effluent stream.

31. The process of claim 1 wherein the washing (d) is conducted at a temperature of at least 80° F. (27° C.).

32. The process of claim 1 wherein the washing (d) is conducted at a temperature of at least 90° F.

33. The process of claim 1 wherein the washing (d) is conducted at a temperature of no more than 120° F. (49° C.).

34. The process of claim 1 wherein the washing (d) is conducted at a temperature of no more than 110° F. (43° C.).

35. The process of claim 1 wherein the washing (d) is conducted at a temperature of no more than 100° F. (38° C.).

36. The process of claim 1 wherein the washing (d) is conducted at a pressure of from about 100 psig to about 350 psig (790 to 2514 kPa).

37. The process of claim 1 wherein the washing (d) is conducted at a pressure of from about 120 psig to about 290 psig (928 to 2101 kPa).

38. The process of claim 1 wherein the washing (d) is conducted at a pressure of from about 140 psig to about 170 psig (1023 to 1273 kPa).

39. The process of claim 1 wherein said fourth vapor effluent stream comprises about 0.5 wt. % or less $C_2$ to $C_6$ carbonyl compounds.

40. The process of claim 1 wherein said fourth vapor effluent stream comprises about 0.1 wt. % or less $C_2$ to $C_6$ carbonyl compounds.

41. The process of claim 1 wherein said fourth vapor effluent stream comprises about 500 ppm wt or less $C_2$ to $C_6$ carbonyl compounds.

42. The process of claim 1 wherein said fourth vapor effluent stream comprises 1.0 wt. % or less of methanol.

43. The process of claim 1 wherein said fourth vapor effluent stream comprises 0.1 wt % or less of methanol.

44. The process of claim 1 wherein said fourth vapor effluent stream comprises 500 ppm wt or less of methanol.

45. The process of claim 1 and further comprising removing acid gas from the fourth vapor effluent stream.

46. The process of claim 45 and further comprising drying the fourth vapor effluent stream such that the dried fourth vapor effluent stream has a dew point of no greater than −150° F. (−101° C.).

47. The process of claim 46 wherein said drying of the fourth vapor effluent stream is conducted after said removing of acid gas therefrom.

48. The process of claim 1 and also comprising fractionating the $C_3$ and $C_4$ hydrocarbons contained in the fourth vapor effluent stream to produce a $C_3$ containing stream and a first $C_4$ containing stream.

49. The process of claim 48 wherein the first $C_4$ containing stream comprises less than 5 wt % $C_3$ and lower hydrocarbons.

50. The process of claim 48 wherein the first $C_4$ containing stream comprises less than 1 wt % $C_3$ and lower hydrocarbons.

51. The process of claim 48 wherein the first $C_4$ containing stream comprises less than 0.1 wt % $C_3$ and lower hydrocarbons.

52. The process of claim 48 wherein said first $C_4$ containing stream comprises less than 5 wt % $C_2$ to $C_6$ carbonyl compounds.

53. The process of claim 48 wherein said first $C_4$ containing stream comprises less than 1 wt % $C_2$ to $C_6$ carbonyl compounds.

54. The process of claim 48 wherein said first $C_4$ containing stream comprises less than 5000 ppm wt $C_2$ to $C_6$ carbonyl compounds.

55. The process of claim 48 wherein said first vapor effluent stream in (a) and said first $C_4$ containing stream further comprise $C_5+$ hydrocarbons and said first $C_4$ containing stream is subjected to further fractionation to separate $C_5+$ hydrocarbons therefrom and create a $C_4$ hydrocarbon product stream.

56. The process of claim 48 wherein said first vapor effluent stream in (a) further comprises dimethyl ether (DME) and wherein said fractionating the $C_3$ and $C_4$ hydrocarbons contained in the fourth vapor effluent stream produces a $C_3$ containing stream and a first $C_4$ and DME containing stream, and said first $C_4$ and DME containing stream is subjected to further fractionation to remove dimethyl ether therefrom and produce said first $C_4$ containing stream.

57. The process of claim 48 wherein said adjusting (b) separates a second liquid $C_4$ containing stream from said first vapor effluent stream and said second liquid $C_4$ containing stream is combined with said first $C_4$ containing stream to produce a third $C_4$ containing stream comprising less than 5 wt % $C_2$ to $C_6$ carbonyl compounds.

58. The process of claim 57 wherein said third $C_4$ containing stream comprises less than 1 wt % of $C_2$ to $C_6$ carbonyl compounds.

59. The process of claim 57 wherein said third $C_4$ containing stream comprises less than 5000 ppm wt $C_2$ to $C_6$ carbonyl compounds.

60. A process for producing olefins comprising:
   (a) contacting an oxygenate feed with a molecular sieve catalyst to produce a vapor product stream comprising $C_2$ and $C_3$ olefins, $C_4$ hydrocarbons, water and oxygenate compounds, including $C_2$ to $C_6$ carbonyl compounds;
   (b) cooling said product stream to condense therefrom a liquid stream rich in water and oxygenate compounds and produce a first vapor effluent stream comprising $C_2$ and $C_3$ olefins, $C_4$ hydrocarbons, and $C_2$ to $C_6$ carbonyl compounds;
   (c) compressing said first vapor effluent stream to produce a second vapor effluent stream having a pressure ranging from about 100 psig to about 350 psig (790 to 2514 kPa) and a temperature ranging from about 700° F. to about 120° F. (21 to 49° C.), said second vapor effluent stream containing about 50 wt. % or more of the $C_4$ hydrocarbons in the first vapor effluent stream;
   (d) washing the second vapor effluent stream with a liquid methanol-containing stream to produce a third vapor effluent stream and a liquid oxygenate-containing methanol stream; and
   (e) washing the third vapor effluent stream with liquid water to produce a fourth vapor effluent stream and an oxygenate-containing water stream, said fourth vapor effluent stream comprising about 1.0 wt. % or less $C_2$ to $C_6$ carbonyl compounds.

61. The process of claim 60 wherein said oxygenate feed comprises methanol and/or ethanol.

62. The process of claim 60 wherein said oxygenate feed comprises methanol.

63. The process of claim 60 wherein said second vapor effluent stream has a pressure ranging from about 120 psig to about 290 psig (928 to 2101 kPa).

64. The process of claim 60 wherein said second vapor effluent stream has a pressure ranging from about 140 psig to about 170 psig (1023 to 1273 kPa).

65. The process of claim 60 wherein said second vapor effluent stream has a temperature ranging from about 80° F. to about 110° F. (27 to 43° C.).

66. The process of claim 60 wherein second vapor effluent stream has a temperature ranging from about 90° F. to about 100° F. (32 to 38° C.).

67. The process of claim 60 wherein the washing (d) is conducted at a temperature of about 80° F. (27° C.) to about 120° F. (49° C.).

68. The process of claim 60 wherein the washing (d) is conducted at a temperature of about 90° F. (32° C.) to about 110° F. (43° C.).

69. The process of claim 60 wherein the washing (d) is conducted at a pressure of from about 100 psig to about 350 psig (790 to 2514 kPa).

70. The process of claim 60 wherein the washing (d) is conducted at a pressure of from about 120 psig to about 290 psig (928 to 2101 kPa).

71. The process of claim 60 wherein the washing (d) is conducted at a pressure of from about 140 psig to about 170 psig (1023 to 1273 kPa).

72. The process of claim 60 wherein the amount of liquid methanol containing stream employed in the washing (d) is about 0.03 lb to about 0.5 lb methanol (as pure methanol) per lb of the second vapor effluent stream.

73. The process of claim 60 wherein the amount of liquid methanol containing stream employed in the washing (d) is about 0.05 lb to about 0.2 lb methanol (as pure methanol) per lb of the second vapor effluent stream.

74. The process of claim 60 wherein the amount of liquid methanol containing stream employed in the washing (d) is about 0.07 lb to about 0.1 lb methanol (as pure methanol) per lb of the second vapor effluent stream.

75. The process of claim 60 wherein the washing (e) is conducted at a temperature of about 80° F. (27° C.) to about 120° F. (49° C.).

76. The process of claim 60 wherein the washing (e) is conducted at a temperature of about 90° F. to about 110° F. (43° C.).

77. The process of claim 60 wherein the washing (e) is conducted at a pressure of from about 100 psig to about 350 psig (790 to 2514 kPa).

78. The process of claim 60 wherein the washing (e) is conducted at a pressure of from about 120 psig to about 290 psig (928 to 2101 kPa).

79. The process of claim 60 wherein the washing (e) is conducted at a pressure of from about 140 psig to about 170 psig (1023 to 1273 kPa).

80. The process of claim 60 wherein at least part of said oxygenate-containing water stream and at least part of said oxygenate-containing methanol stream are fractionated to produce an oxygenate-rich overhead stream and a water-rich liquid bottoms stream.

81. The process of claim 80 wherein at least a part of said oxygenate-rich overhead stream is recycled for said contacting (a).

82. The process of claim 80 wherein at least a part of said water-rich liquid bottoms stream is recycled for use as said liquid water in said washing (e).

83. The process of claim 60 wherein at least a part of said liquid stream rich in water from (b) is fractionated to produce an oxygenate-rich overhead stream and a water-rich liquid bottoms stream.

84. The process of claim 80 wherein at least a part of said oxygenate-rich overhead stream is recycled for said contacting (a).

85. The process of claim 80 wherein at least a part of said water-rich liquid bottoms stream is recycled for use as said liquid water in said washing (e).

* * * * *

UNITED STATES PATENT AND TRADEMARK OFFICE
CERTIFICATE OF CORRECTION

PATENT NO. : 7,332,639 B2 Page 1 of 1
APPLICATION NO. : 10/871394
DATED : February 19, 2008
INVENTOR(S) : Keith H. Kuechler, Jeffrey L. Brinen and Philip A. Ruziska It is certified that error appears in the above-identified patent and that said Letters Patent is hereby corrected as shown below:

In column 20, line 20, In Claim 1, step (b), "700°F." should read --70°F--

In column 23, line 24, In Claim 60, step (c), "700°F." should read --70°F--

Signed and Sealed this

Fifth Day of August, 2008

JON W. DUDAS
*Director of the United States Patent and Trademark Office*